United States Patent [19]

Ten Haken et al.

[11] 4,358,446
[45] Nov. 9, 1982

[54] USE AS FUNGICIDES OF N-(3-PYRIDYLMETHYL)-N-ACYL ANILINES

[75] Inventors: Pieter Ten Haken, Eastling, Nr. Faversham; Shirley B. Webb, Sheidwich, Nr. Faversham, both of England

[73] Assignee: Shell Oil Company, Houston, Tex.

[21] Appl. No.: 269,173

[22] Filed: Jun. 2, 1981

Related U.S. Application Data

[63] Continuation-in-part of Ser. No. 164,975, Jul. 1, 1980, abandoned.

[30] Foreign Application Priority Data

Jul. 19, 1979 [GB] United Kingdom ............... 7925164

[51] Int. Cl.³ .................... A01N 43/40; A01N 55/02
[52] U.S. Cl. .................. 424/245; 424/263; 546/9; 546/337
[58] Field of Search ............ 424/263, 245; 546/337, 546/334

[56] References Cited

U.S. PATENT DOCUMENTS

| | | | |
|---|---|---|---|
| 2,731,470 | 1/1956 | Elslager et al. | 546/334 X |
| 3,055,906 | 9/1962 | Shapiro et al. | 546/337 |
| 4,172,893 | 10/1979 | Weiler | 424/263 |

*Primary Examiner*—Leonard Schenkman

[57] ABSTRACT

Use as fungicides of N-(3-pyridylmethyl)-N-acyl anilines, of the formula

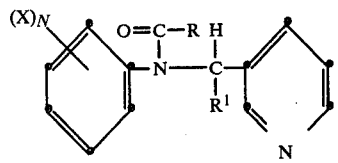

wherein the symbols have assigned meanings.

1 Claim, No Drawings

USE AS FUNGICIDES OF N-(3-PYRIDYLMETHYL)-N-ACYL ANILINES

This application is a continuation-in-part of application Ser. No. 164,975, filed July 1, 1980 abandoned.

DESCRIPTION OF THE INVENTION

It has been found that useful fungicidal properties are possessed by certain N-(3-pyridylmethyl)-N-acyl anilines, of the formula:

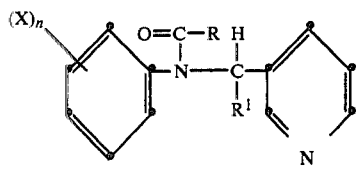

wherein R is hydrogen, or is alkyl or alkoxyalkyl of from one to six carbon atoms, $R^1$ is hydrogen or alkyl of from one to four carbon atoms, X is halogen and n is zero, one or two.

This invention thus provides a method for combatting fungi at a locus which comprises applying to that locus a fungicidally effective amount of a compound of Formula I. In particular, the invention provides a method for combatting barley powdery mildew.

Compounds of Formula I form N-oxides; acid addition salts with acids, for example mineral acids such as sulphuric or hydrochloric acid or organic acids such as citric or tartaric acid; and complexes with metal salts, for example complexes of the compound of Formula I with a salt, for example a halide, of calcium, copper or iron, in the ratio of 2:1, 1:1 or 1:2. The use of such derivatives forms part of the present invention, and the derivatives may be prepared from compounds of Formula I by methods analogous to known methods.

In the method according to the invention, the compound of Formula I or acid addition salt, N-oxide or metal salt complex thereof, is suitably applied to the locus to be treated at a dosage in the range of from 0.1 to 3 kilogram per hectare. Most conveniently it is applied in the form of a composition containing the compound together with one or more suitable carriers.

These fungicidal compounds can be prepared by acylating a compound of the general formula

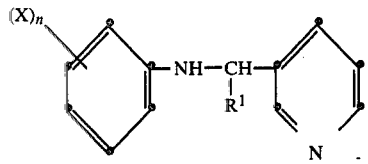

in which $R^1$ and $X_n$ have the meanings given for the compounds of Formula I, using a suitable acylating agent to introduce the R—C(O)—moiety.

Any suitable acylating agent, for example a carboxylic acid or an acid anhydride or, preferably, acid halide, derived from a carboxylic acid, may be used. Acid chlorides are especially suitable, and the reaction is then preferably carried out in the presence of an acid binding agent, which may be an organic or inorganic base. Organic amines, for example triethylamine, are especially suitable acid-binding agents. The reaction is preferably carried out in the presence of an insert solvent, for example a hydrocarbon such as benzene, at a temperature in the range of from 50° to 150° C., preferably 60° to 100° C. The reaction is conveniently carried out under reflux.

The compound of Formula II may for example be prepared by reduction of a compound of the general formula:

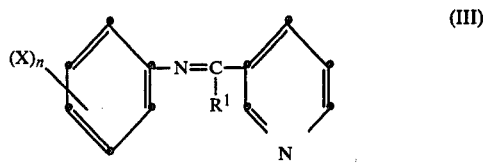

in which $R^1$ and $X_n$ have the meanings given for the compounds of Formula I. The reduction may for example be carried out using gaseous hydrogen and a catalyst, or using formic acid. When formic acid is used the reaction conditions may be chosen such that at least some of the compound of formula II produced is formylated in situ, thus directly producing a compound of the general formula I in which $R^1$ represents a formyl group starting from a compound of Formula III.

The compound of Formula III may be prepared by methods analogous to methods known in the art, for example by coupling a compound of the general formula:

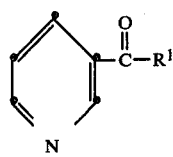

with a compound of the general formula:

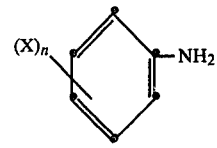

The method of combatting fungi according to the invention is suitably carried out using a composition which comprises the active compound together with a suitable carrier. The invention therefore also provides a biologically active composition which comprises a novel compound according to the invention together with a suitable carrier. Preferably the amount of active ingredient in the composition is in the range of from 0.05 to 95% by weight of the composition.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating agricultural compositions may be used.

Suitable solid carriers include natural and synthetic clays and silicates, for example natural silicas such as diatamaceous earths; magnesium silicates, for example talcs; magnesium aluminium silicates, for example attapulgites and vermiculites; aluminium silicates, for example kaolinites, montmorillonites and micas; calcium carbonate; calcium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilizers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethyene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3-10% w of a dispersing agent and, where necessary, 0-10% w of stabilizer(s) and/or other additives such as penetrants or stickers. Dusts are usually formulated as a dust concentrate having a similar compositions to that of a wettable powder but without a dispersant, and are diluted in the field with further solid carrier to give a composition usually containing ½-10% w of active ingredient. Granules are usually prepared to have a size between 10 and 100 BS mesh (1.676-1.152 mm), and may be manufactured by agglomeration or impregnation techniques. Generally, granules will contain ½-25% w active ingredient and 0-10% w of additives such as stabilizers, slow release modifiers and binding agents. Emulsifiable concentrates usually contain, in addition to a solvent and, when necessary, co-solvent, 10-50% w/v active ingredient, 2-20% w/v emulsifiers and 0-20% w/v of other additives such as stabilizers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilizers, penetrants and stickers, and water or an organic liquid in which the active ingredient is substantially insoluble; certain organic solids or inorganic salts may be present dissolved in the formulation to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients, for example, other compounds possessing insecticidal, herbicidal, plant growth regulating or fungicidal properties.

The following Examples illustrate the invention.

In each of these examples, the identity of each intermediate and product was confirmed by appropriate chemical and spectral analyses.

EXAMPLE 1

4-Chloro-N-(3'-pryidylmethyl)-N-trimethylacetyl Aniline (1)

To a stirred solution of 3.0 g of trimethylacetyl chloride in 50 ml of dry benzene under nitrogen was added a solution of 2.5 g of dry trimethylaniline in 25 ml of dry benzene, followed by 4.9 g of 4-chloro-N-(3'-pyridylmethyl)-aniline. (Prepared by the method of V. Carelli, et al., Farmaco (Pavia) Ed. Sci., 16, 375-386 (1961)). The mixture was stirred and heated under reflux for 6.5 hours; then cooled, and washed with water and the organic phase dried over anhydrous MgSO$_4$. After filtration, the solvent was removed under reduced pressure and the residue crystallized from hexane to give 1, as a crystalline solid, m.p.: 82°-3° C.

EXAMPLES 2 TO 11

Using methods analogous to those described in Example 1, the following further individual compounds of the invention were prepared.

TABLE I

| Example No. | In Formula I: $(X)_n$ | R | $R^1$ | Melting Point C |
|---|---|---|---|---|
| 2 | 4-fluoro | -t-butyl | H | 103-105 |
| 3 | 4-chloro | —CH$_2$OCH$_3$ | H | Oil |
| 4 | 4-chloro | —CH$_2$.t-butyl | H | 75-76 |
| 5 | 2,4-dichloro | -t.butyl | H | 45-47 |
| 6 | 3,4-cichloro | -t.butyl | H | 63-65 |
| 7 | 2,4-difluoro | -t.butyl | H | 73.5-75.5 |
| 8 | 3-chloro-4-fluoro | -t.butyl | H | 61-62 |
| 9 | -(n = 0) | -t.butyl | H | 38-40 |
| 10 | 4-bromo | -t.butyl | H | 90-92 |
| 11 | 4-chloro | -t.butyl | CH$_3$ | Oil |

EXAMPLE 12

The fungicidal activity of compounds of Formula I was investigated by means of the following tests:

(a) Activity against vine downy mildew (Plasmopera viticola-Pv.a.)

The test was a direct anti-sporulant one using a foliar spray. The lower surfaces of leaves of whole vine plants, were inoculated by spraying with an aqueous suspension containing $10^5$ zoosporangia/milliliter 4 days prior to treatment with the test compound. The inoculated plants were kept for 24 hours in a high humidity compartment, 48 hours at glasshouse ambient temperature and humidity and then returned for a further 24 hours to high humidity. The plants were then dried and infected leaves detached and sprayed on the lower surfaces at a dosage of 1 kilogram of active material per hectare using a track sprayer. After drying the petioles of the sprayed leaves were dipped in water and the leaves returned to high humidity for a further 72 hours incubation, followed by assessment. Assessment was based on the percentage of the leaf area covered by sporulation compared with that on control leaves.

(b) Activity against vine downy mildew (Plasmopera viticola-Pv.t.)

The test was a translaminar protectant one using a foliar spray. The upper surfaces of leaves of whole vine plants were sprayed at a dosage of 1 kilogram of active material per hectare using a track sprayer. The lower surfaces of the leaves were then inoculated, up to 6 hours after treatment with the test compound, by spraying with an aqueous suspension containing $10^5$ zooporangia/milliliter. The inoculated plants were kept for 24 hours in a high humidity compartment, 4 days at glasshouse ambient temperature and humidity and then returned for a further 24 hours to high humidity. Assessment was based on the percentage of the leaf area covered by sporulation with that on control leaves.

(c) Activity against vine grey mould (Botrytis cinerea-B.c.)

The test was a direct eradicant one using a foliar spray. The under-surfaces of detached vine leaves were inoculated by pipetting ten large drops of an aqueous suspension containing $5 \times 10^5$ conidia/milliliter on to them. The inoculated leaves were kept uncovered overnight during which time the fungus has penetrated the leaf and a visible necrotic lesion might be apparent where the drop was made. The infected regions were sprayed directly with a dosage of 1 kilogram of active material per hectare using a track sprayer. When the spray had dried the leaves were covered with petri dish lids and the disease allowed to develop under the moist conditions. The extent of the necrotic lesion beyond the original drop together with the degree of sporulation was compared with that on control leaves.

(d) Activity against potato late blight (Phytophthora infestans-P.i.e.)

The test was a direct eradicant one using a foliar spray. The upper surfaces of the leaves of potato plants (12–18 centimeter high, in monopots) were inoculated by spraying with an aqueous suspension containing $5 \times 10^3$ zoosporangia/milliliter 16–19 hours prior to treatment with the test compound. The inoculated plants were kept overnight at high humidity and then allowed to dry before spraying at a dosage of 1 kilogram of active material per hectare using a track sprayer. After spraying the plants were returned to high humidity for a further period of 48 hours. Assessment was based on a comparison between the levels of disease on the treated and control plants.

(e) Activity against potato late blight (Phytophthora infestans-(P.i.p.)

The test measured the direct protectant activity of compounds applied as a foliar spray. Tomato plants, Cultivar Ailsa Craig, 1–15 centimeters high, in monopots were used. The whole plant was sprayed at a dosage of 1 kilogram of active material per hectare using a track sprayer. The plant was then inoculated up to 6 hours after treatment with the test compound, by spraying with an aqueous suspension containing $5 \times 10^3$ zoosporangia/milliliter. The inoculated plants were kept in high humidity for 3 days. Assessment was based on a comparison between the levels of disease on the treated and control plants.

(f) Activity against barley powdery mildew (Erysiphe graminis-E.g.)

The test measured the direct anti-sporulant activity of compounds applied as a foliar spray. For each compound about 40 barley seedlings were grown to the one-leaf stage in a plastic pot of sterile potting compost. Inoculation was effected by dusting the leaves with conidia of *Erysiphe graminis*, spp. hordei. 24 hours after inoculation the seedlings were sprayed with a solution of the compound in a mixture of acetone (50%), surfactant (0.04%) and water using a track sprayer. The rate of application was equivalent to 1 kilogram of active material per hectare. First assessment of disease was made 5 days after treatment, when the overall level of sporulation on the treated pots was compared with that on control pots.

(g) Activity against wheat brown rust (Puccinia recondita-P.r.)

The test was a direct antisporulant one using a foliar spray. Pots containing about 25 wheat seedlings per pot, at first leaf stage were inoculated by spraying the leaves with an aqueous suspension, containing $10^5$ spores/milliliter plus a little Triton X-155 (Trade Mark), 20–24 hours before treatment with the compound under test. The inoculated plants were kept overnight in a high humidity compartment, dried at glass-house ambient temperature and then sprayed at a dosage of 1 kilogram of active material per hectare using a track-sprayer. After treatment the plants were kept at glass-house ambient temperature and assessment made about 11 days after treatment. Assessment was based on the relative density of sporulating pustules per plant with that on control plants.

(h) Activity against broad bean rust (Uromyces fabe-U.f.)

The test was a translaminar antisporulant one using foliar spray. Pots containing 1 plant per pot were inoculated by spraying an aqueous suspension, containing $5 \times 10^4$ spores/milliliter plus a little Triton X-155, onto the undersurface of each leaf 20–24 hours before treatment with test compound. The inoculated plants were kept overnight in a high humidity compartment, dried at glass-house ambient temperature and then sprayed, on the leaf upper surface, at a dosage of 1 kilogram per hectare of active material using a track sprayer. After treatment the plants were kept at glasshouse temperature and assessment made 11–14 days after treatment. Symptoms were assessed on the relative density of sporulating pustules per plant compared with that on control plants.

(i) Activity against rice leaf blast (Pyricularia oryzae-P.o.)

The test was a direct eradicant one using a foliar spray. The leaves of rice seedlings (about 30 seedlings per pot) were sprayed with an aqueous suspension containing $10^5$ spores/milliliter 20–24 hours prior to treatment with the test compound. The inoculated plants were kept overnight in high humidity and then allowed to dry before spraying at a dosage of 1 kilogram of active material per hectare using a track sprayer. After treatment the plants were kept in a rice compartment at 25°–30° C. and high humidity. Assessment was made 4–5 days after treatment and was based on the density of necrotic lesions and the degree of withering when compared with control plants.

(j) Activity against rice sheath blight (Pellicularia sasakii-P.s.)

The test was a direct eradicant one using a foliar spray. 20–24 hours prior to treatment with the test compound rice seedlings (about 30 seedlings per pot) were sprayed with 5 millileters of an aqueous suspension containing 0.2 grams of crushed sclerotia/mycelium per milliliter. The inoculated plants were kept overnight in a humid cabinet maintained at 25°–30° C., followed by spraying at a dosage of 1 kilogram of active material per hectare. The treated plants were then returned to high humidity for a further period of 3–4 days. With this disease brown lesions are seen that start at the base of the sheath and extend upwards. Assessments were made on the number and extent of the lesions when compared with the control.

The extent of disease control is expressed as a control rating according to the criteria:

0 = less than 50% disease control
1 = 50–80% disease control
2 = greater than 80% disease control/S1 and /S2 indicate systemic activity, using the same scale of rating. The obtained control ratings are set out in Table II.

TABLE II

| Compound of Example No. | Fungicidal Activity | |
|---|---|---|
| | B.c | E.g. |
| 1 | | 2 |
| 2 | | 2 |
| 3 | 2 | 2/1S |
| 4 | | 2 |

EXAMPLE 13

Further compounds of Formula I were tested for fungicidal activity against the same species as described in Example 12 except that tests on the two following species replaced tests on *Pellicularia sasakii*.

(k) Activity against apple powdery mildew (Podosphaera leuco-tricha, P.l.)

The test measured that direct anti-sporulant activity of compounds applied as a foliar spray. For each compound, apple seedlings were grown to the three to five leaf stage in a plastic pot of sterile potting compost. Inoculation was effected by spraying the leaves with a suspension in water of conidia of the test species. 48 hours after inoculation the seedlings were sprayed with a solution of the test compound in a mixture of acetone (50%), surfactant (0.04%) and water using a track sprayer. The rate of application was equivalent to 1 kilogram active material per hectare. First assessment of disease was made 10 days after treatment, when the overall level of sporulation on the treated pots were compared with those on control pots.

(l) Activity against peanut leaf spot (Cercospora arachidicola-C.a.)

The procedure of (k) above was repeated using peanut seedlings grown to height of about 15 centimeters. Assessment of disease was made 14 days after treatment. The results of the tests of Example 13 are given in Table III below.

TABLE III

| Compound of Example No. | B.c. | E.g. | P.r. | U.f. | P.l. |
|---|---|---|---|---|---|
| 5 | | 2 | 2 | 2 | 2 |
| 6 | 2 | 2 | | | 2 |
| 7 | | 2/2S | | 1 | 2 |
| 8 | | 2 | 1 | | |
| 9 | | | 2 | | 1 |
| 10 | | 2/1S | | 1 | |
| 11 | | 2 | | | |

We claim:

1. A method for combatting fungi at a locus which comprises applying to the locus a fungicidal amount of a compound of the formula:

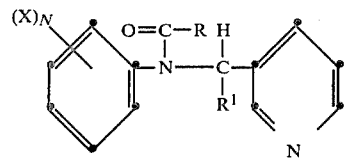

wherein R is hydrogen, or is alkyl or alkoxyalkyl of from one to six carbon atoms, $R^1$ is hydrogen or alkyl of from one to four carbon atoms, X is halogen and n is zero, one or two, the acid addition salts thereof, N-oxides thereof and complexes thereof with halides of calcium, copper and iron.

* * * * *